United States Patent
Eckert et al.

(10) Patent No.: US 8,492,610 B1
(45) Date of Patent: Jul. 23, 2013

(54) TRANSGENEIC ANIMAL EXPRESSING A MULTIPLE MUTATED FORM OF PRESENILIN 1

(75) Inventors: Anne Eckert, Mannheim (DE); Walter Muller, Worms-Herrnsheim (DE); Christian Czech, Grenzach-Wyhlen (DE); Laurent Pradier, Verriéres (FR); Gunter Tremp, Palaiseau (FR)

(73) Assignee: Aventis Pharma S.A., Antony (FR)

( * ) Notice: Subject to any disclaimer, the term of this patent is extended or adjusted under 35 U.S.C. 154(b) by 489 days.

(21) Appl. No.: 10/088,139

(22) PCT Filed: Sep. 22, 2000

(86) PCT No.: PCT/FR00/02623
§ 371 (c)(1),
(2), (4) Date: Dec. 17, 2002

(87) PCT Pub. No.: WO01/22811
PCT Pub. Date: Apr. 5, 2001

Related U.S. Application Data

(60) Provisional application No. 60/181,306, filed on Feb. 9, 2000.

(30) Foreign Application Priority Data

Sep. 27, 1999 (FR) .................................... 99 12017

(51) Int. Cl.
*G01N 33/00* (2006.01)
*A01K 67/00* (2006.01)
*A01K 67/27* (2006.01)
*C12N 5/07* (2010.01)

(52) U.S. Cl.
USPC ...................... 800/3; 800/8; 800/18; 435/325

(58) Field of Classification Search
USPC .................... 800/3, 8, 9, 12, 14, 18; 435/325
See application file for complete search history.

(56) References Cited

U.S. PATENT DOCUMENTS 5,859,308 A * 1/1999 Mirochnitchenko et al. ..... 800/9
6,395,960 B1 * 5/2002 St. George-Hyslop et al. 800/18

FOREIGN PATENT DOCUMENTS

| WO | WO 9817782 | 4/1998 |
|---|---|---|
| WO | WO 9851781 | 11/1998 |

OTHER PUBLICATIONS

Hammer et al. 1990, Cell, 6: 1099-1112.*
Cameron 1997, Molecular Biotechnology, 7: 253-265.*
Mench 1999, Transgenic Animals in Agriculture, eds. Murray et al., CAB International: Oxon, pp. 251-268.*
Nilsberth et al., 1999, The Histochemical Journal, 31: 515-523.*
Leutner et al., 2000, Neuroscience Letters, 292: 87-90.*
Marjaux et al., 2004, Neuron, 42: 189-192.*
Wengenack et al., 2000, Nature Biotechnology, 18: 868-872.*
Bell and Dockrell, 2003, JEADV, 17: 178-183.*
Badley et al., 1996, Journal of Virology, 70: 199-206.*
LePage, 1998, The Journal of Nutrition, 129: 620-627.*
Auerbach, 2004, Acta Biochimica Polonica, 51: 9-31.*
Cowan et al. 2003, Xenotransplantation, 10: 223-231.*
Hammer et al. 1986, J. of Anim. Sci., 63: 269-278.*
Racay, 2002, Bratisl Lek Listy, 103: 121-126.*
Delibas et al., 2002, Clinical Biochemistry, 32: 137-141.*
Lovell et al., 2000, Free Radical Biology and Medicine, 28: 418-427.*
Citron et al., 1998, Neurobiology of Diseases, 5: 107-116.*
Ishii et al., 1997, Neuroscience Letters, 228: 17-20.*
Borchelt et al., 1997, Neuron, 19: 939-945.*
Xia et al., 1997, The Journal of Biological Chemistry, 272: 7977-7982.*
Lombardi et al., 1999, Journal of Neuroimmunology, 97: 163-171.*
Eckert et al, Society for Neuroscience Abstracts, 1999, 25:1846, Poster 426.6.*
Eckert, "Enhanced vulnerability to cell death in lymphocytes from PS-1 mutant transgenic mice", Society for Neuroscience Abstracts, vol. 25, No. 1-2, 1999, p. 1846.
Czech, "Characterization of human presenilin 1 transgenic rats: Increased sensitivity to apoptosis in primary neuronal cultures", Neuroscience, vol. 87, No. 2, Nov. 1998, pp. 325-336.
Lamb, "Amyloid production and deposition in mutant amyloid precursor protein and presenilin-1 yeast artificial chromosome transgenic mice", Nat. Neurosci., vol. 2, No. 8, Aug. 1999, pp. 695-697.
Leutner, "Altered antioxidant enzyme activity and radical oxygen formation in PS-1 mutant transgenic mice", Society for Neuroscience Abstracts, vol. 25, No. 1-2, 1999, p. 1857.
International Search Report WO 01/22811 A1 dated Apr. 5, 2001.

* cited by examiner

*Primary Examiner* — Anoop Singh
*Assistant Examiner* — Chi-Feng Hsu
(74) *Attorney, Agent, or Firm* — Lathrop & Gage LLP

(57) ABSTRACT

The present invention relates to the field of transgenic animal models and more particularly the animal models of Alzheimer's disease. The invention relates to a transgenic animal expressing a multimutated form of presenilin 1 and allowing an apoptotic phenomenon to be detected in a renewable peripheral tissue.

2 Claims, 11 Drawing Sheets

TRANSGENEIC ANIMAL EXPRESSING A MULTIPLE MUTATED FORM OF PRESENILIN 1

Figure 1:
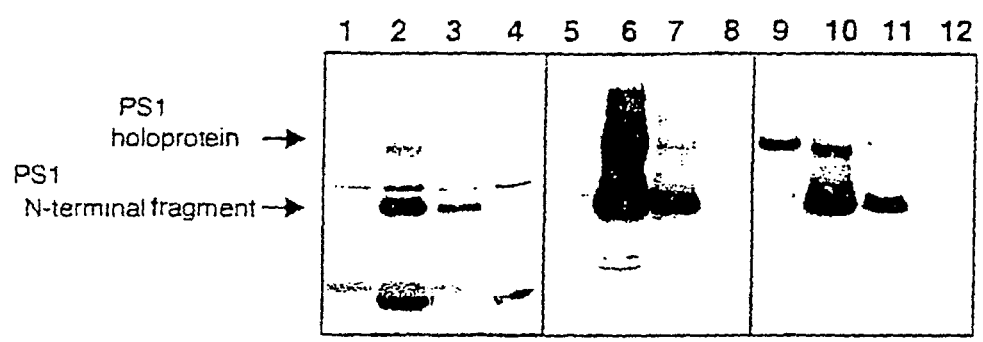

The present invention relates to the field of transgenic animal models and more particularly the animal models of Alzheimer's disease. The invention relates to a transgenic animal expressing a multimutated form of presenilin 1 and allowing an apoptotic phenomenon to be detected in a renewable peripheral tissue.

Alzheimer's disease (AD) is a progressive neurodegenerative disease which affects a large proportion of the elderly population. This disease is characterized at the clinical level by a loss of memory and a decline in cognitive functions, and at the neuropathological level by the presence in the brain of intracellular neurofibrillary deposits and extracellular deposits of the β-amyloid (Aβ) peptide forming the amyloid plaques (Yanker et al., 1996) as well as a pronounced neuronal loss. In addition to these signs, there are a large number of other abnormal changes including an impairment of the mechanisms of protection against free radicals.

Amyloid plaques are mainly composed of the Aβ peptides containing 40 or 42 residues which are generated during the proteolytic process for the β-amyloid peptide precursor protein (APP). The extracellular deposits of Aβ are very specific for AD and for associated disorders. They represent the early and invariable feature of all the forms of AD, including the familial forms (FAD). The FADs appear relatively early (between 40 and 60 years of age) and are due to mutations in the APP gene in 5% of FAD cases with six identified single or double missense mutations; in the presenilin 1 (PS 1) gene in 50 to 70% of FAD cases with more than 40 different mutations identified to date; and in the presenilin 2 (PS 2) gene in rarer cases of FAD with 2 missense mutations described (for a review see Price and Sisodia, 1998). Mutations in these three genes have been demonstrated to induce changes in the proteolysis of APP, which lead to an overproduction of Aβ, especially of the long form Aβ42, and to the early appearance of the pathology and symptoms which are similar to those of the sporadic forms of AD.

In the transgenic animal models described to date, the symptomotology of neuronal loss comparable to AD is expressed only at the level of the neurons or in their direct vicinity and in particular the phenomenon of apoptosis (Chiu et al., 1999). However, these models have several disadvantages including in particular the need to breed a very large number of animals, most often over long periods of time, which may be up to 24 months, in order to monitor the appearance of the symptoms of AD, the systematic sacrificing of the animals to study the pathology and thus experimental protocols which are particularly tedious and expensive.

No animal model of AD therefore exists which makes it possible to measure the symptoms and, in particular, the phenomena of cell death associated with AD in peripheral tissues.

The present invention therefore results from the search for a new animal model representative of the neuropathology which makes it possible to measure the symptoms associated with AD, and in particular apoptosis, in peripheral tissues.

A first subject of the invention therefore relates to a transgenic animal model of Alzheimer's disease expressing multimutated presenilin 1.

Transgenic animal is understood to mean any nonhuman animal exhibiting a modification of its genome. The modification of the genome may result from an impairment or a modification of one or more genes by "knock-in" or by "knock-out". This modification may be due to the action of conventional impairing or mutagenic agents or may be performed by site-directed mutagenesis, as is described in Materials and Methods.

The modification of the genome may also result from an insertion of a gene or of genes or from replacement of a gene or of genes in its (their) wild-type or mutated form.

The modifications of the genome are advantageously carried out on reproductive stem cells and preferably on the pronuclei.

In the context of the present invention, the animal model is advantageously a mammal. In particular, it may be a mouse, a rat or a rabbit obtained according to conventional transgenesis techniques. By way of example illustrating one of the methods of transgenesis, there may be mentioned the method of microinjection of an expression cassette comprising the modified genes into the two fertilized pronuclei, as is described in Materials and Methods.

In this regard, the animal model of the invention is obtained by injecting an expression cassette comprising a nucleic acid. Preferably, this nucleic acid is a DNA which may be a genomic DNA (gDNA) or a complementary DNA (cDNA).

In the context of the model of the invention, the DNA encodes any PS1 gene such that the cells of the animal model express the multimutated protein.

The sequence of the nonmutated human PS1 protein was described by Sherrington et al in 1995. Multimutated protein is understood to mean the PS1 protein comprising at least three mutations which are combined or associated with each other, that is to say which are present at the same time in the said protein. According to a preferred embodiment of the invention, the DNA encodes the PS1 gene which comprises 5 mutations (PS1M5).

The mutations in the PS1 gene may be one of the 40 mutations described to date in the literature. Preferably, the mutations in the PS1 gene are M146L, H163R, A246E, L286V, C410Y, I143T, L235P, P264L, P267S, E317G, G384A, L392V, A426P and/or P436S. They are in partial combination with each other.

The mutations M146L, H163R, A246E, L286V, C410Y, combined with each other, are preferred for producing a model according to the invention.

In the context of the model of the invention, the DNA is placed under the control of sequences allowing its expression and in particular of transcription promoter sequences.

As promoter sequences, there may be mentioned most particularly the HMG promoter (Gautier et al., 1989), as well as the PDGF promoter (Sasahara et al., 1991), the Thy-1 promoter (Lüthi et al., 1997) and the Prion gene promoter (Scott et al., 1992).

According to a particularly advantageous embodiment of the invention, the animal model comprises the PS1 gene having the M146L, H163R, A246E, L286V, C410Y mutations, placed under the control of the HMG promoter.

The animal model according to the invention is very advantageous because it corresponds to a practical model which is representative of the phenomena of cell death in AD. Indeed, this model exhibits symptoms associated with AD including in particular apoptosis of the cells and oxidative stress and makes it possible, in addition, to measure these symptoms in the cells of renewable peripheral tissues. It should be noted that oxidative stress also manifests itself in the brain of these animals. Renewable peripheral tissues should be understood to mean any tissue exhibiting a renewal of these cells over time. By way of example of renewable peripheral tissue, there may be mentioned the spleen, the liver, blood and the like.

Preferably, the apoptotic phenomenon is measured in blood cells and still more preferably in the lymphocytes. Among the lymphocytes, the T lymphocytes are preferred for the invention.

Thus, the results described in the examples demonstrate that the transgenic mouse expressing the multimutated PS1 develops cellular impairments which are found in Alzheimer's disease and, in particular, exhibits increased sensitivity to apoptosis. This phenomena is moreover not observed with a simple natural pathological mutant of the M146L type. This phenotype is specifically obtained with a nonnatural form grouping together several individual mutations, and preferably 5 mutations, on the same cDNA. In addition, through the ectopic expression of the transgene by virtue of the ubiquitous promoter, this model makes it possible to detect an apoptotic phenomenon (linked to the mutations in Alzheimer's disease) in a renewable peripheral tissue. This model therefore provides a much more practical source of material (not requiring sacrificing the animal), therefore allowing longitudinal monitoring.

Furthermore, the impairments of the metabolism of calcium and of the free radicals which are observed very clearly in this model are similar to the increase in the latent period for the calcium response and the oxidative stress which are observed with Alzheimer patients (Eckert et al., 1997 and 1998), which reinforces the relevance of this model.

The present invention therefore also relates to the use of the animal model, as described above, for the detection of compounds intended for the treatment of neurodegenerative diseases, preferably Alzheimer's disease.

Indeed, through its advantageous properties, this model allows, in comparison with known models, the detection of compounds which are particularly suitable for the treatment of AD, in particular as described in humans.

These compounds may be chemical molecules, peptide or protein molecules, antibodies, chimeric molecules as well as antisense DNAs or ribozymes.

The compounds which are detected may be used as a medicament, as they are or in combination with a pharmaceutically acceptable vehicle in order to obtain a pharmaceutical composition. This may include in particular isotonic, sterile saline solutions (monosodium or disodium phosphate, sodium, potassium, calcium or magnesium chloride and the like, or mixtures of such salts), or dry, in particular freeze-dried, compositions which, upon addition, depending on the case, of sterilized water or of physiological saline, allow the constitution of injectable solutions. The injections may be carried out by the stereotaxic, topical, oral, parenteral, intranasal, intravenous, intramuscular, subcutaneous, intraocular or transdermal route, and the like.

The detection of the compounds described above is based on bringing the animal model of the invention into contact, especially by an administration such as for example an injection, with a compound or a mixture of compounds presumed to have an action and then measuring the effect(s) of the compounds in particular at the level of the peripheral tissues of the model on the different biochemical and/or histological changes such as for example those described in the Methods and Results section including apoptosis, the level of intracellular calcium, the level of free radicals and the like.

Another subject of the invention relates to a cell extracted from the animal model as described above as well as its use for the detection of compounds intended for the treatment of neurodegenerative diseases, preferably Alzheimer's disease.

The detection of compounds described above is based on bringing cells extracted from the animal model of the invention into contact with a compound or a mixture of compounds presumed to have an action and then measuring the effect(s) of the compounds at the level of the whole cells, in cell homogenates or on a subcellular fraction, on different parameters such as cell death, the production of the Aβ peptide, production of free radicals, and the like.

The results described in the examples demonstrate the advantages of the model of the invention and clearly support the use of this transgenic model as a simple and rapid measuring and monitoring tool in the context of therapeutic strategies such as in particular the development of antiapoptotic agents or of agents limiting cell death linked to AD more generally.

The present invention will be described in greater detail with the aid of the examples which follow but which should be considered as illustrative and nonlimiting.

LEGEND TO THE FIGURES

FIG. 1: Analysis of the expression of human PS1 in the transgenic mice PS1M5 (lanes 1, 5, 9), PS1M146L (lanes 2, 6, 10), PS1wt (lanes 3, 7, 11) and non.transgenic (lanes 4, 8, 12). The transgenic mouse tissues: lymphocytes (lanes 1-4), spleen (lanes 5-8) and brain (lanes 9-12), were lysed and analysed by immunoblotting using an antibody specific for the human sequence of PS1 (epitope in the N-term region of PS1). The holoprotein PS1 (approx. 50 kDa) as well as the N-terminal fragment are observable. The expression of the transgene is observable for the three transgenic mice. There is absence of endoproteolytic cleavage for the protein PS1M5.

Figure 2:
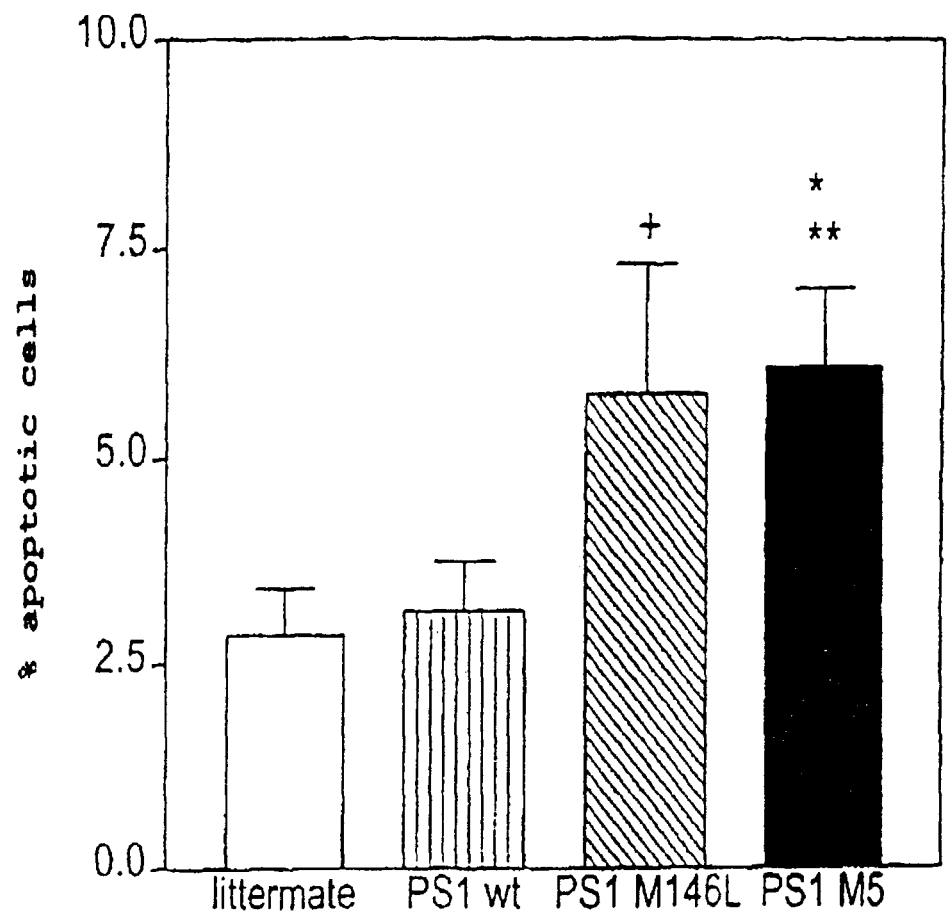

FIG. 2: Increased apoptosis of the lymphocytes derived from transgenic mice PS1M146L and PS1M5 under basal conditions. The levels of apoptosis under basal conditions were measured in dissociated lymphocytes. The PS1M5 lymphocytes show a higher level of apoptosis compared with PS1wt (*, $p<0.05$) or with the nontransgenic littermate controls (**, $p<0.05$)). The same applies to the PS1M146L lymphocytes compared with the littermate controls (+, $p<0.05$).

Figure 3:
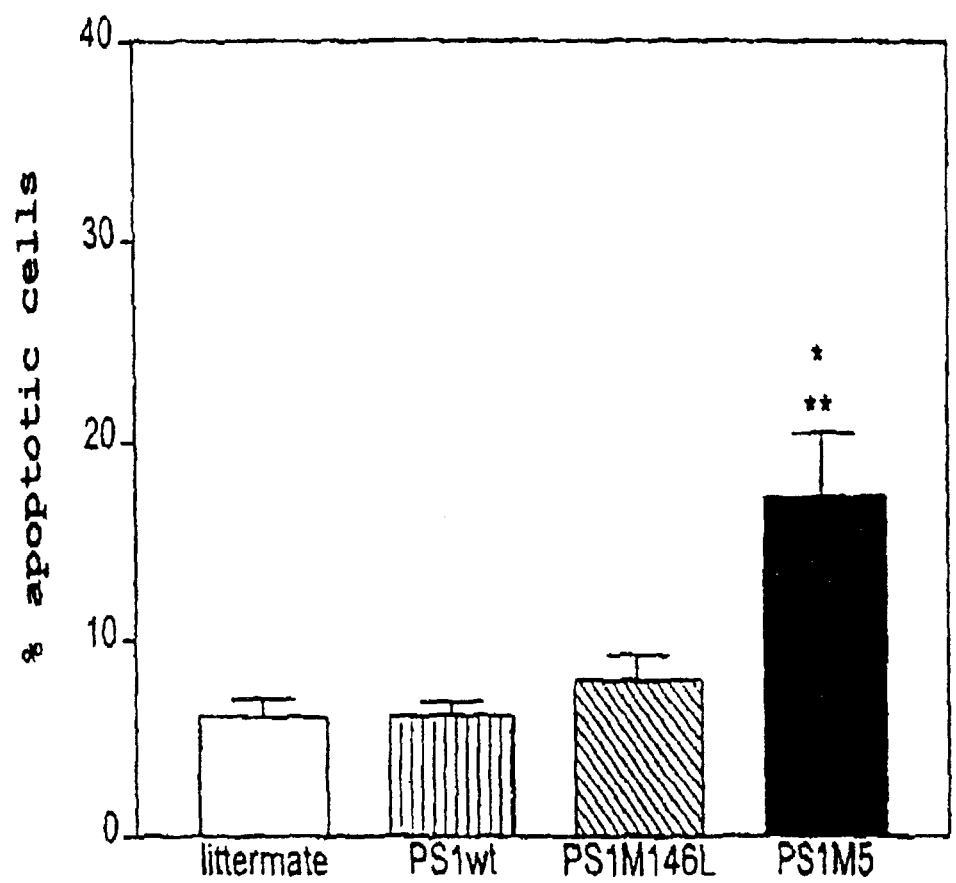

FIG. 3: Apoptosis after 2.5 h of incubation of lymphocytes derived from transgenic mice. After 2.5 h of incubation, the PS1M5 lymphocytes show a significantly higher level of apoptosis (***, $p<0.001$) compared with PS1wt, PS1M146L or with the nontransgenic controls (littermates).

Figure 4:
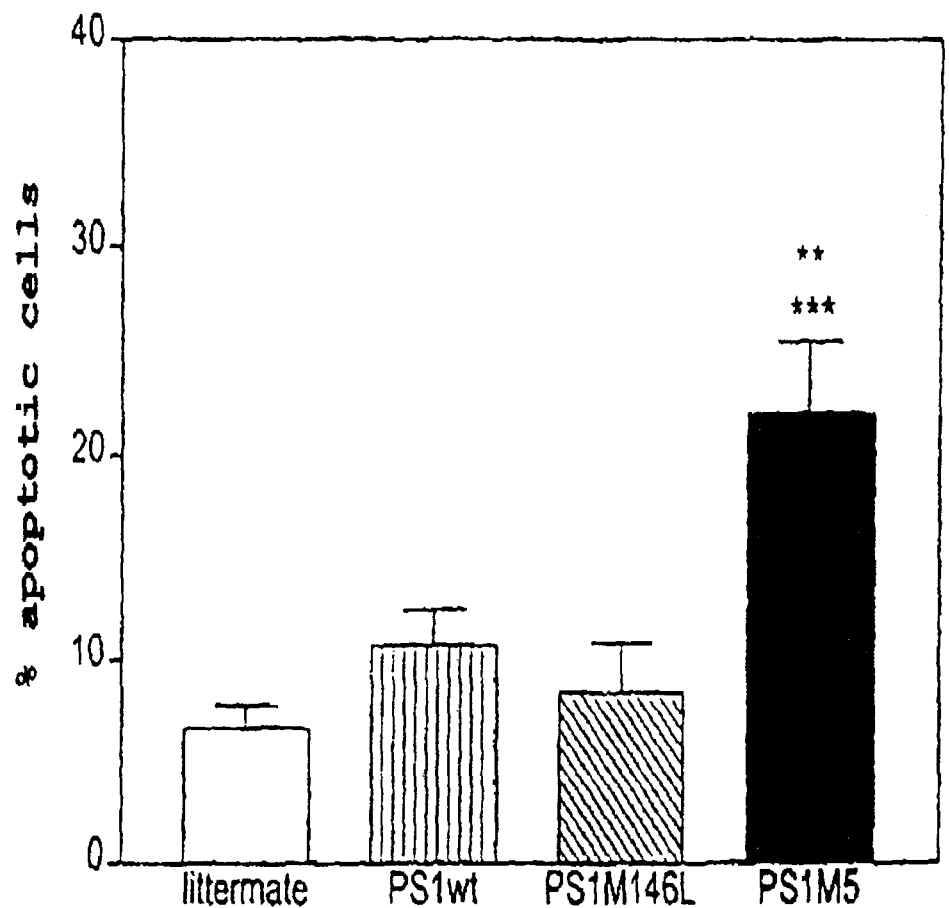

FIG. 4: Apoptosis induced by deoxyribose treatment of lymphocytes derived from transgenic mice. After induction with deoxy-D-ribose (10 mM), the apoptosis levels are significantly higher in the PS1M5 group than in the other groups (, $p<0.01$ vs PS1wt and PS1M146L; *, $p<0.001$ vs littermates).

Figure 5:
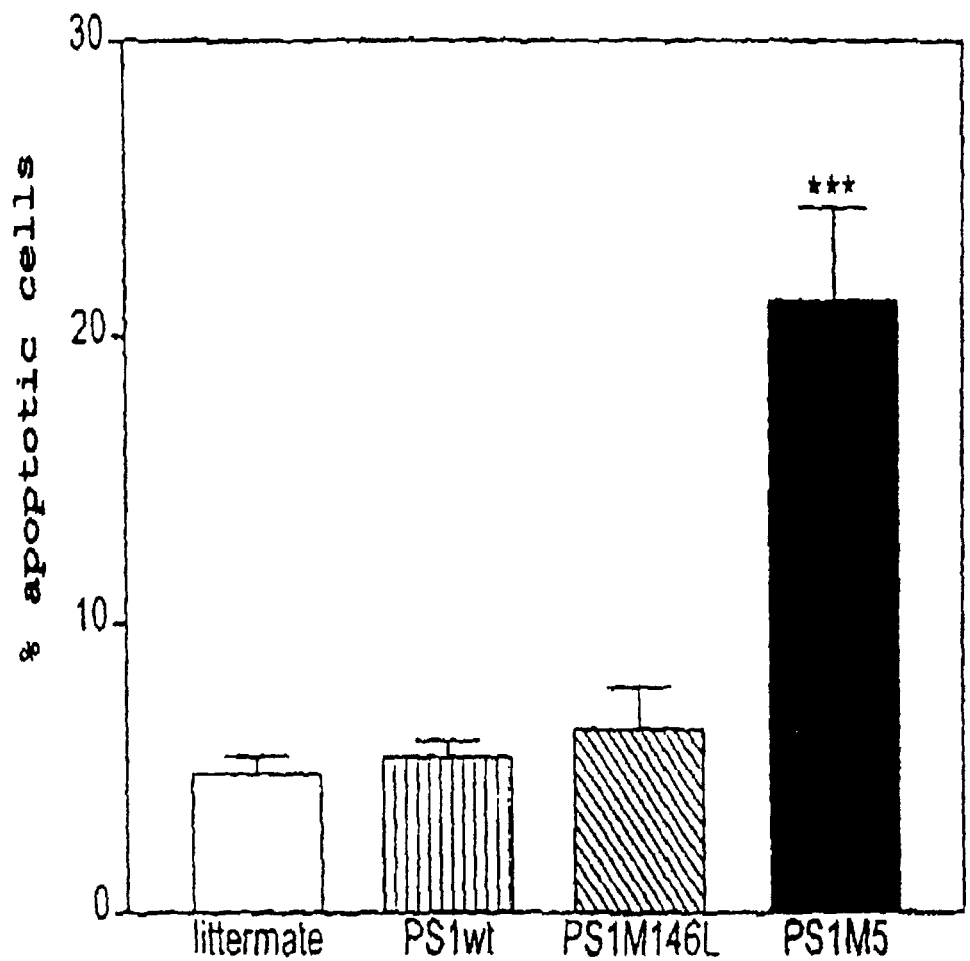

FIG. 5: Apoptosis induced by hydrogen peroxide treatment of lymphocytes derived from transgenic mice. After induction with hydrogen peroxide (1 mM), the apoptosis levels are significantly higher in the PS1M5 group than in the other groups (***, $p<0.001$). There is no difference between the other groups.

Figure 6:
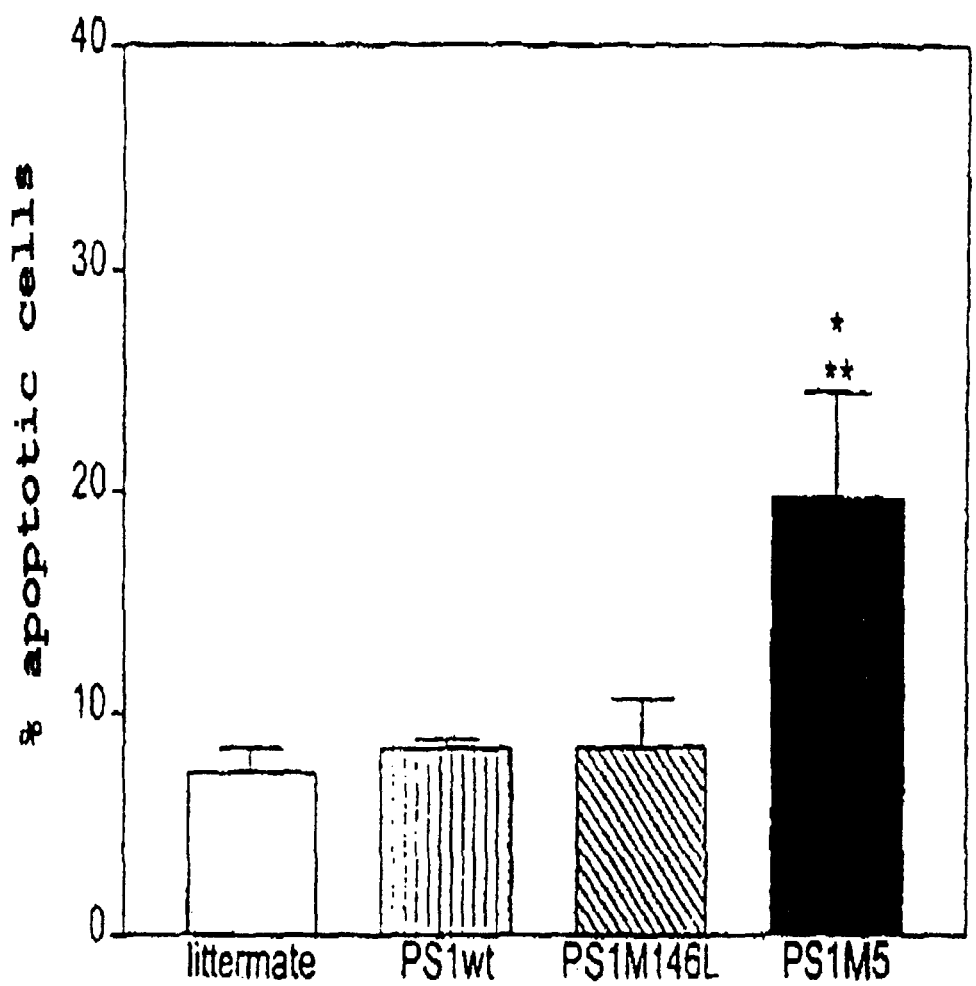

FIG. 6: Apoptosis induced by dexamethasone treatment of lymphocytes derived from transgenic mice. After induction with dexamethasone ($10^{-7}$ M), the apoptosis levels are significantly higher in the PS1M5 group than in the other groups (*, $p<0.05$ vs PS1M146L and littermates; **, $p<0.01$ vs PS1 wt). There is no difference between the other groups.

Figure 7:
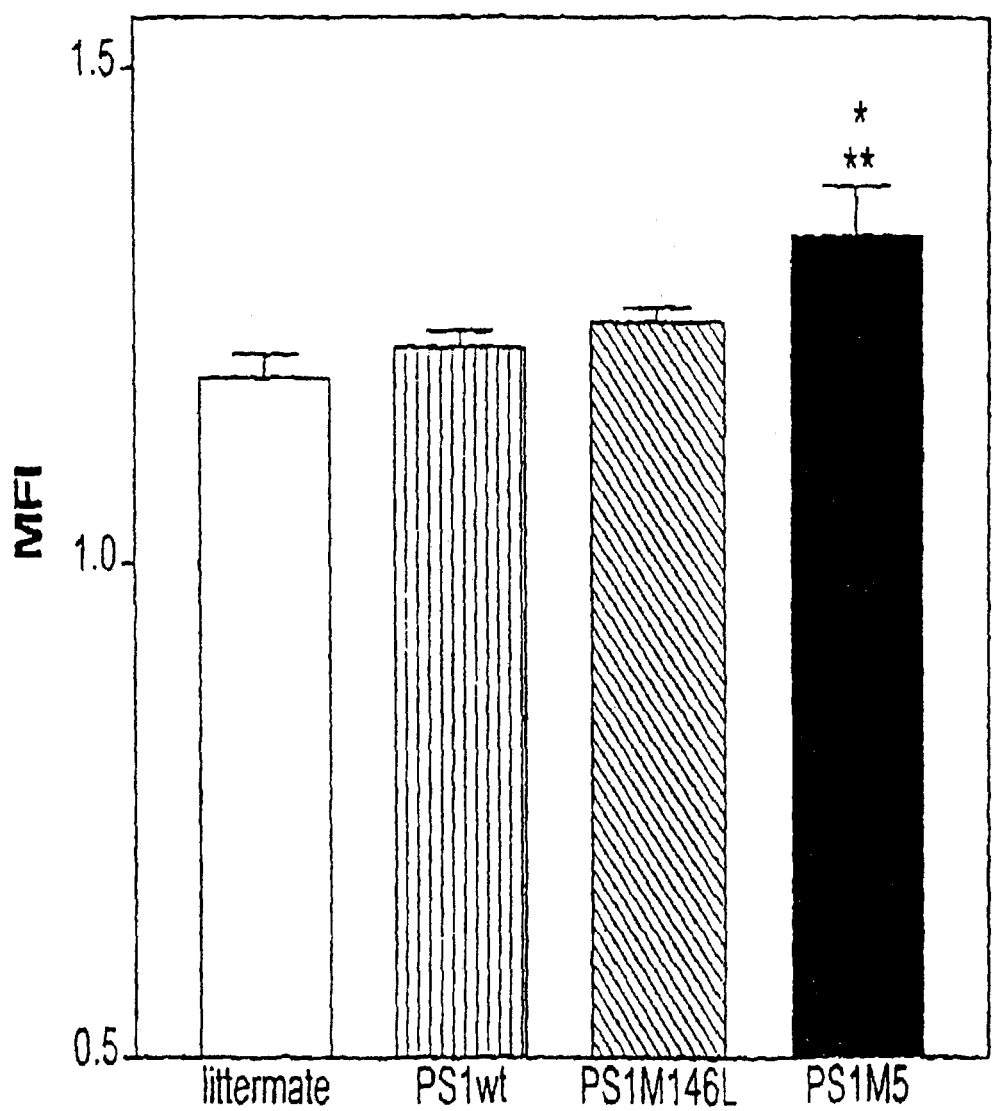

FIG. 7: Increase in the levels of free radicals in the lymphocytes of transgenic mice PS1M5. The levels of the oxygenated radical species (Reactive Oxygen Species) were measured in the mouse lymphocytes by flow cytometry (Rhodamine 123) and expressed as mean fluorescence intensity (MFI). The levels of ROS are significantly higher in the lymphocytes of transgenic mice PS1M5 compared with the other groups (*, p<0.05 vs PS1wt; **, p<0.01 vs littermates).

Figure 8:
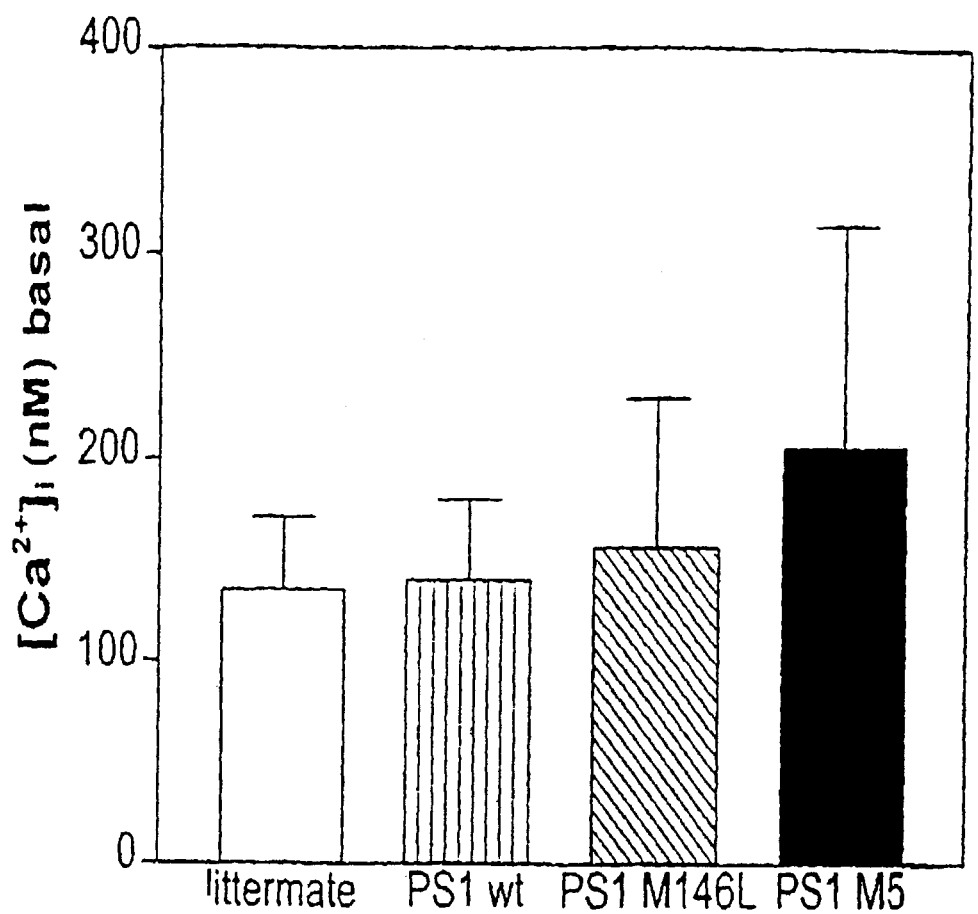

FIG. 8: Increased mobilization of intracellular calcium in the lymphocytes of transgenic mice PS1M5. The levels of $[Ca^{2+}]_i$ were determined under resting (basal) conditions. The levels of intracellular calcium are higher in the lymphocytes of transgenic mice PS1M5 than in the other groups. There is no difference between the other groups.

Figure 9:
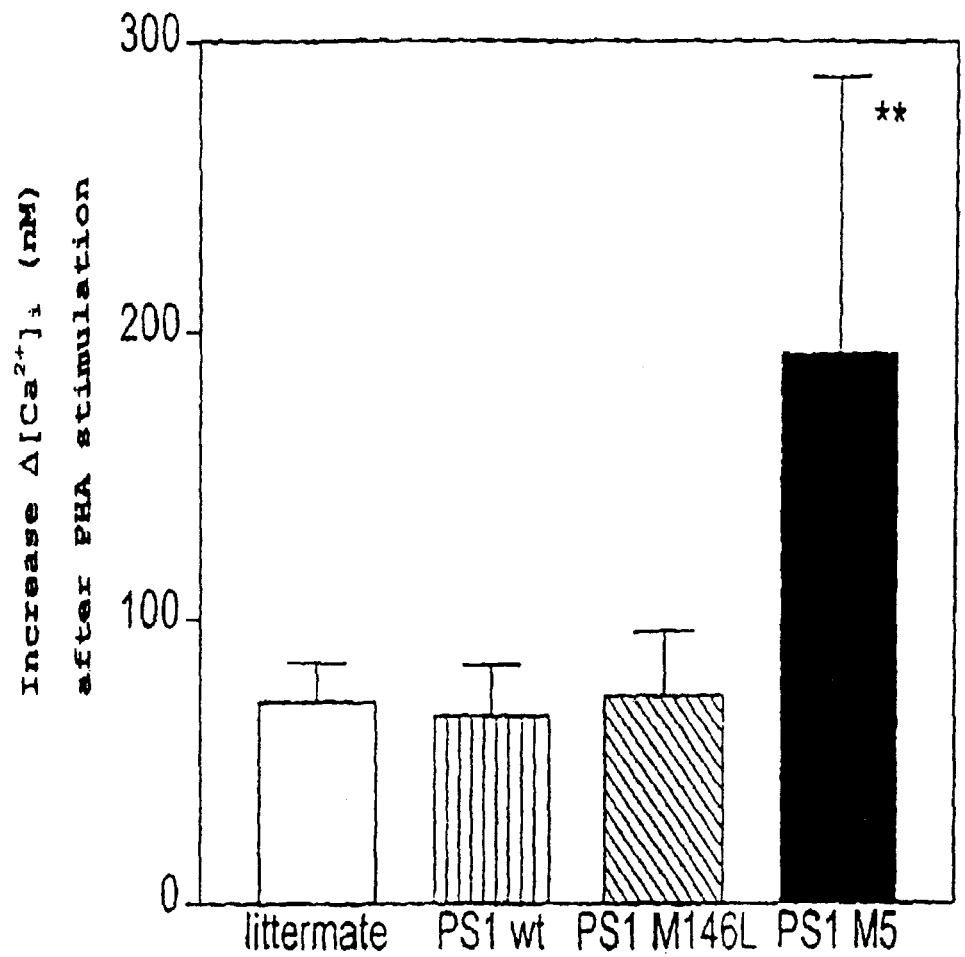

FIG. 9: Increased intracellular calcium response after stimulation with PHA in the lymphocytes of transgenic mice PS1M5. The difference between the levels of $[Ca^{2+}]_i$ after and before mitogenic stimulation with PHA (15 microg/ml) has been represented. The lymphocytes of transgenic mice PS1M5 respond more strongly to the stimulus than the other groups (p<0.01). There is no difference between the other groups.

Figure 10:
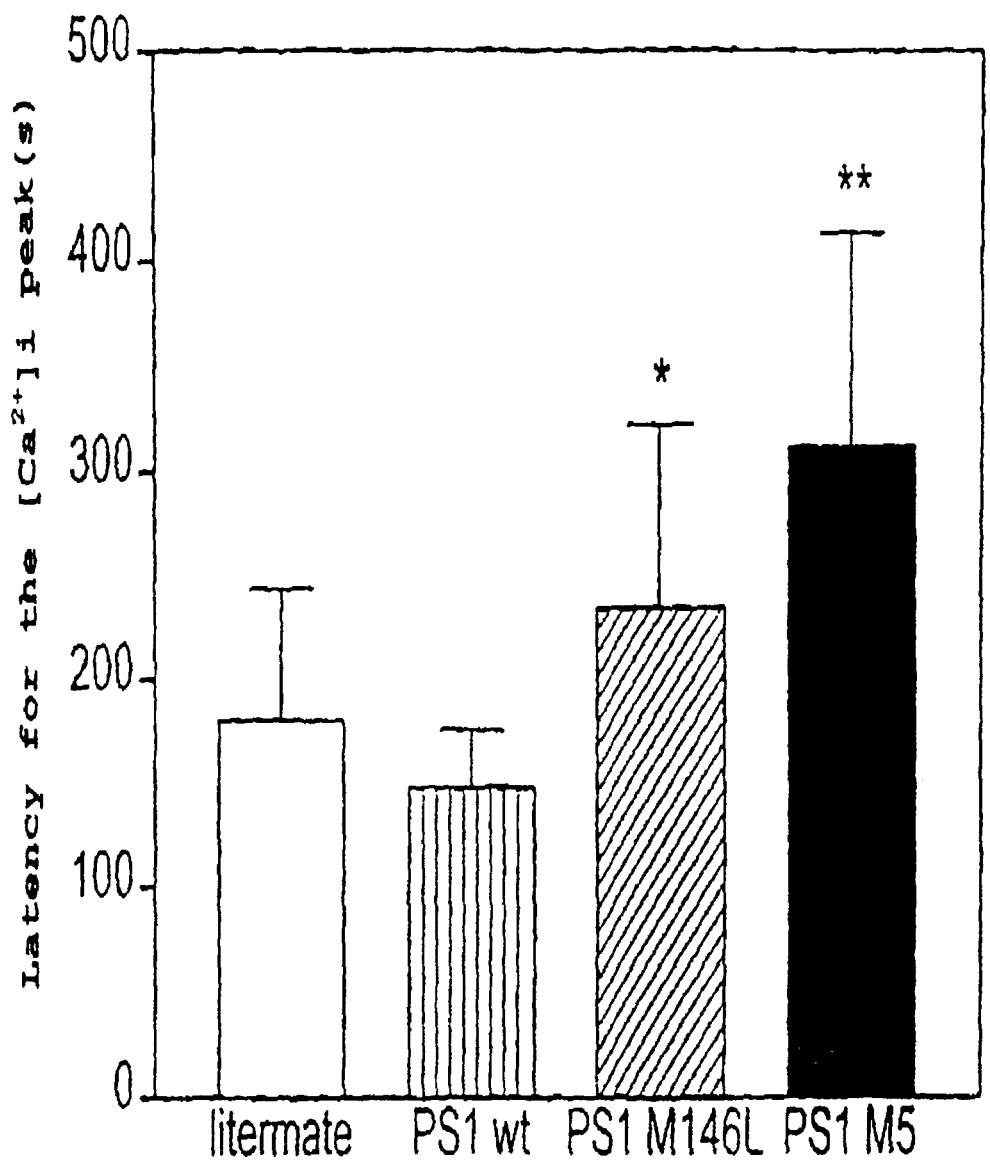

FIG. 10: Latency for the slower mobilization of intracellular calcium in the lymphocytes of transgenic mice PS1M5 and PS1M146L. The time interval to reach the peak for $[Ca^{2+}]_i$ after mitogenic stimulation with PHA is higher in the lymphocytes of transgenic mice PS1M5 (**, p<0.05 vs PS1wt and littermates) as well as to a lesser degree for the transgenic mice PS1M146L (*, p<0.05 vs PS1wt). There is no difference between the mouse PS1wt and the nontransgenic controls (littermates).

FIG. 11: Effect of the human mutations of PS1 in the brain of transgenic mice on the mechanisms of protection of the free radicals. A) Levels of activity of the enzyme superoxide dismutase, SOD. B) Levels of activity of the enzyme glutathione reductase. C) Levels of lipid peroxidation after stimulation with $FeCl_3$. A significant reduction in the mechanisms of detoxification of the free radicals (SOD and GR) is observed in the brain of the transgenic mice PS1M5 (*, p<0.05 vs PS1wt; **, p<0.05 vs PS1M146L) with a tendency towards reduction in the mice PS1M146L. Conversely, the levels of stimulated lipid peroxidation (due to the presence of free radicals) is increased in the mice PS1M5.

MATERIALS AND METHODS

1. Mutagenesis of Presenilin 1-PS1

The human cDNA for PS1 containing a Kozak consensus at the level of the initial ATG has been previously described (Pradier et al., 1999). The mutagenesis of PS1 was carried out using the Sculptor™ in vitro mutagenesis kit (Amersham, France). The coding region of PS1 was subcloned into the vector Bluescript (stratagene) and a single-stranded DNA prepared. The 5 mutations used in the context of the invention were introduced with the aid of oligonucleotides containing the desired mutations according to the supplier's instructions:
M146L, 5'GAGGATAGTCG*TGACAACAAT3'; SEQ ID No. 1
H163R, 5'AAGCCAGGCC*TGGATGACCTT3'; SEQ ID No. 2
A246E, 5'GATGAGCCAT*GCAGTCCATTG3'; SEQ ID No. 3
L286V, 5'GGAGTAAATGC*GAGCTGGAA3'; SEQ ID No. 4
C410Y, 5'GGCTACGAAT*CAGGCTATGGT3'; SEQ ID No. 5
the * denotes the position of the nucleotide mutation introduced on the complementary strand. To obtain the construct containing the five combined mutations (PS1M5 for multimutant 5), five successive mutageneses were carried out. The entire sequence of the PS1 cDNA was checked on each mutagenesis to ensure the absence of undesirable mutations.

2. Generation and Identification of the Transgenic Mice

For the construction of the transgenes, the cDNAs for PS1 wild type, PS1M146L and PS1M5 were subcloned into the SmaI/BamHI restriction sites of the multiple cloning site of the transgenic expression vector HMG (Czech et al., 1997). The cDNAs are under the control of the HMG-CoA reductase partial promoter which allows ubiquitous expression of the transgene. For the microinjection, the expression cassette was purified by gel electrophoresis after restriction with the enzyme NotI in order to eliminate the unimportant sequences from the vector. The purified transgene was taken up at the final concentration of 2.5 ng/microl in 10 mM Tris-HCl (pH 7.4), 0.1 mM EDTA and injected into one of the two pronuclei of fertilized mouse oocytes. The surviving embryos are transplanted into the oviduct of an adoptive mother. The presence of the transgene was analysed by PCR and Southern. The PCR was carried out using oligonucleotides specific for the human PS1 sequence having the sequences SEQ ID No. 6 5'-TAA TTG GTC CAT AAA AGG C-3' and SEQ ID No. 7 5'-GCA CAG AAA GGG AGT CAC AAG-3', generating an amplification fragment of 550 bp. For the Southern analysis, a 1.2 kb PstI-SalI fragment, corresponding to the first intron of the HMG expression cassette was labeled with alpha-$^{32}$P and used as probe for the detection of the transgene and of the endogenous HMG-CoA reductase gene. By virtue of the latter analysis, the absence of any major rearrangement or of any deletion within the transgene may be guaranteed. The mice were bred in accordance with the French rules for caring for animals.

3. Immunoblotting

The cerebral tissue and the spleen of transgenic mice (PS1wt, PS1M146L and PS1M5) and of nontransgenic control mice (littermate) were homogenized on ice in a 0.32 M sucrose solution containing protease inhibitors (Complete™, Boehringer-Mannheim, Germany). The cellular debris were removed by centrifugation at 4° C. for 5 min at 1500 g. The lymphocyte lysates were prepared in the same manner from the fraction of purified cells. The protein concentration in the supernatant was measured with the aid of the BCA protein test (Pierce, USA). For the detection of PS1, 25 μg of protein extract were incubated at 56° C. for 20 min in the Laemmli loading buffer containing 8M urea and 50 mM dithiothreitol. The proteins were fractionated by polyacrylamide gel electrophoresis (SDS-PAGE). After transferring the proteins onto nitrocellulose filter (Amersham, France) the filter was heated in PBS for 5 min in order to increase the sensitivity and immediately saturated with 5% (w/V) of powdered skimmed milk in TBS 50 mM Tris-HCl pH 8.1, 150 mM NaCl, 0.05% (V/V) Tween 20 for 1 h and incubated overnight at 4° C. with the human anti-PS1 primary antibody (Ab), MAB1563 (Chemicon, USA), diluted 1/10,000 in TBS buffer alone. The binding of the Ab was detected with an anti-IgG Ab conjugated with horseradish peroxidase (Amersham, France) followed by a chemiluminescence detection system (Amersham, France) according to the manufacturer's instructions.

4. Preparation of the Lymphocytes

The lymphocytes were prepared from freshly dissociated mouse spleen. The spleen is homogenized in RPMI buffer and then the homogenate is passed through a 10-micron filter. The cellular homogenate is washed several times by centrifugation and resuspension. After lysis of the erythrocytes present, the number of cells is determined by counting under a microscope.

To obtain the T lymphocytes, the B cells were counterselected by attachment onto magnetic beads carrying anti-B cell antibodies (Dynabeads Mouse pan B, Dynal, Norway) and separation of the beads. The remaining cells are T lymphocytes (CD3-positive) at more than 80% as determined by flow cytometric analysis.

5. Measurement of Apoptosis

To determine the content of DNA at the G1 phase, which defines the percentage of apoptotic cells, after treatment at various times, the T lymphocytes are separated by centrifugation and the cellular pellets taken up in lysis buffer (0.1% sodium citrate, 0.1% Triton X-100) containing 50 µg/ml of propidium iodide (Sigma, Munich). The samples are stored at 4° C. for 1-2 hours before flow cytometric analysis (FACS-Calibur, Benckton Dickinson, Cell Quest software). Cell death was induced by various treatments: 2-deoxy-D-ribose (d-Rib, 10 mM), hydrogen peroxide ($H_2O_2$, 1 mM) and dexamethasone (dex, $10^{-7}$ M) for 2.5 h. Cell death determined in the absence of treatment was defined as in vitro spontaneous apoptosis.

6. Measurement of Intracellular Calcium

The T cell fraction is taken up in RPMI buffer and incubated in the presence of Fura-2-AM (Molecular Probe, Leiden, The Netherlands). The incubation is terminated by addition of HBSS buffer and washing of the suspension by centrifuging several times in order to remove the dye from the medium. The T cell fraction is finally taken up in HBSS buffer and stored on ice until the measurement of intracellular calcium.

The Fura-2 fluorescence was measured as previously described (Eckert et al., 1993) using an SLM-Aminco luminescence spectrometer with wavelengths of excitation at 340 nm and 380 nm and of emission at 510 nm. The intracellular concentration of calcium $[Ca^{2+}]_i$ was calculated from the method of ratios of Grynkiewicz as previously described (Eckert et al., 1997) using a Kd value of 224 nM. As stimulator of calcium mobilization in the lymphocytes, PHA-P (Sigma, Munich) was added at the concentration of 15 micrograms/ml.

7. Measurement of the Free Radicals

The production of free radicals (ROS) was quantified by flow cytometry (FACSCalibur, Benckton Dickinson) using dihydrorhodamine-123 (DHR, Molecular Probes) as fluorescent revealing agent. The cells are resuspended in 1 ml of HBSS buffer in the presence of DHR (final concentration 10 microM) and incubated at 37° C. for 15 min on a shaking bath. The conversion of DHR to its fluorescent derivative rhodamine-123 is then quantified and expressed as mean fluorescence intensity (MFI).

8. Preparation of the Cerebral Tissue

The mice were used at the age of 3-4 months and sacrificed by decapitation. The brains were removed and washed extensively in buffer on ice. The tissue (cerebellum included) was weighed and immediately frozen at −20° C. The tissue was homogenized with the aid of a Potter-Elvehjem homogenizer in Tris-HCl buffer at 5 and 20 mM, respectively, in order to obtain homogenates diluted (weight/volume) 1/10 and 1/5 respectively.

9. Test of CuZn SOD and Glutathione Reductase Activity

The brain homogenates (1/5 w/v) were centrifuged at 8500×g for 10 minutes at 4° C. The supernatant was used to measure the SOD and glutathione reductase (GS) activities. The SOD activity was measured with the aid of an SOD-525 type kit (Calbiochem, Germany). This kit uses a specific reagent (R1) which undergoes alkaline auto-oxidation which is accelerated by superoxide dismutase. A second reagent (R2) is used to eliminate the interference caused by mercaptans, such as glutathione. One unit of SOD-525 activity is defined as the activity doubling the level of auto-oxidation of R1. The GR activity was similarly assayed with the aid of a specific kit (Calbiochem, Germany). This kit measures the level of oxidation of NADPH to NADP+ which is accompanied by a reduction in absorbance at 340 nm which is detected by spectrophotometry. One unit of GR activity is defined by the reduction of one micromole of GSSG at 25° C., pH 7.6.

10. Measurement of the Basal and Stimulated Lipid Peroxidation (LPO) in the Cerebral Tissues The brain homogenates (1/10, w/v) are incubated in buffer containing (stimulated LPO) or otherwise (basal LPO) $FeCl_3$ and 100 µM for 30 min at 37° C. in a stirred aqueous bath. After incubation, the homogenates are centrifuged at 3000×g for 10 min. The supernatants are used to detect lipid peroxidation by measuring the concentration of malondialdehyde (MDA) with the aid of an LPO-586 type kit (Calbiochem). This kit uses a specific chromophore which reacts with MDA at moderate temperature (45° C.).

EXAMPLES

Example 1

Immunodetection of the Proteins Corresponding to the Transgenes PS1wt, PS1M146L and PS1M5

Transgenic mice PS1wt, PS1M146L and PS1M5 (multimutant) were generated. The transgene is under the control of the human HMG-CoA reductase promoter, a housekeeping gene which confers a high ubiquitous expression including the brain (Gautier et al., 1989, Czech et al., 1997 and 1998). Analysis of the levels of expression of the transgenes (human PS1) was carried out on the spleen and brain tissues as well as on the lymphocytic cell fraction with the aid of an antibody specific for the human PS1 sequence not recognizing the mouse homologue (FIG. 1). In the brain (FIG. 1, lanes 9-12), the N-terminal fragment of PS1 is the predominant species with higher levels for PS1M146L compared with PS1wt. For PS1M146L, the holoprotein (complete protein, approx. 50 kDa) is detectable, demonstrating a saturation of the endoproteolysis process at high expression of PS1 as previously described. On the other hand, for PS1M5, the multimutant, there is complete absence of endoproteolysis and only the holoprotein is detectable. Similar results were observed in the spleen and the lymphocytes with variable but detectable levels of expression in all these tissues.

Example 2

Enhanced Spontaneous Apoptosis in the Lymphocytes Isolated from Multimutated PS1 Transgenic Mice The aim of this example is to demonstrate that the peripheral cells of the animal model expressing the multimutated PS1 exhibits an enhanced spontaneous apoptosis which is persistent over time.

The lymphocytes isolated from transgenic mice expressing PS1wild type (without mutation) have the same level of basal apoptosis (2.8%) as the nontransgenic controls derived from the same litter (littermate) (FIG. 2). On the other hand, this spontaneous apoptosis is greatly increased (6%) in the transgenic mice expressing the mutation PS1-M146L or the multimutation PS1M5.

Very interestingly, after culturing for 2.5 h without apoptotic stimulus, the levels of spontaneous apoptosis for the lymphocytes of PS1M5 were higher than for PS1wt or the simple mutant PS1M146L or the nontransgenic controls (FIG. 3).

These results demonstrate that the cells of the transgenic animal of the invention and in particular those of the peripheral tissues (lymphocytes in particular) exhibit not only a greater spontaneous apoptosis compared with the controls but also that it persists over time.

Example 3

Increase in Apoptosis Induced by Treatment with Deoxyribose in the Lymphocytes Derived from PS1M5 Transgenic Mice The aim of this example is to demonstrate the apoptosis induced by deoxyribose is much greater in the multimutant PS1 mouse model.

After induction by treatment with 2-deoxy-D-ribose (d-Rib), the levels of apoptosis are significantly greater for the transgenic lymphocytes PS1M5 than for PS1wt, simple mutant PS1-M146L or the nontransgenic controls (FIG. 4).

This increase in apoptosis after induction demonstrates an enhanced response (sensitization) to an apoptotic stress due to the expression of multimutant PS1. Combined with an increase in basal apoptosis, these results clearly indicate that the transgenic expression of a multimutated form of PS1 causes a much higher sensitivity to apoptosis in the lymphocytes and the like.

Example 4

Increase in Apoptosis Induced by Treatment with Hydrogen Peroxide in the Lymphocytes Derived from PS1M5 Transgenic Mice The aim of this example is to demonstrate that the apoptosis induced by hydrogen peroxide is much greater in the multimutant PS1 mouse model.

After stimulation by treatment with hydrogen peroxide (H202), the levels of apoptosis are significantly greater in the lymphocytes PS1M5 than for the others which are transgenic or nontransgenic ($p<0.001$, FIG. 5). There is no significant difference between the transgenic lymphocytes PS1 wt (S182) and simple mutant PS1M146L or the nontransgenic controls.

This increase in apoptosis after induction by a different stress demonstrates the general nature of the hypersensitivity to apoptosis observed in this model.

Example 5

Increase in Apoptosis Induced by Treatment with Dexamethasone in the Lymphocytes Derived from PS1M5 Transgenic Mice The aim of this example is to demonstrate that the apoptosis induced by a treatment with dexamethasone is much greater in the multimutant PS1 mouse model.

Likewise, after stimulation with dexamethasone, the levels of apoptosis are significantly greater in the lymphocytes PS1M5 than for the others which are transgenic or nontransgenic ($p<0.01$, FIG. 6). There is no significant difference between the transgenic lymphocytes PS1wt and simple mutant PS1M146L or the nontransgenic controls.

This increase in apoptosis after induction by a third different stress confirms the general natural of the hypersensitivity to apoptosis conferred by the transgenic expression of multi-mutated PS1 (but not simple mutant).

Example 6

Increase in the Levels of Free Radicals in the Lymphocytes of PS1M5 Transgenic Mice The levels of oxygenated free radical agents (Reactive Oxygen Species) were measured in the mouse lymphocytes by flow cytometry. The ROS levels are significantly higher in the lymphocytes of transgenic mice PS1M5 ($p<0.05$) compared with the other groups (FIG. 7). There is no significant difference between the other groups although a trend towards an increase in the ROS levels appears between the littermate controls and the transgenics PS1wt and PS1M146L.

This increase in the ROS levels demonstrates that it is possible to detect, under basal conditions, in this model an impairment of a biochemical parameter (greatly affected in AD) which may underlie the hypersensitivity to apoptosis.

Example 7

Enhanced Mobilization of Intracellular Calcium in the Lymphocytes of PS1M5 Transgenic Mice Because apoptosis is modulated by the intracellular levels of calcium, these were analysed in the lymphocytes of the transgenic mice. At rest, the levels of $[Ca^{2+}]_i$ for the controls and the transgenic mice PS1wt and PS1M146L are identical (less than or equal to about 150 nM). The multiple mutant PS1M5 demonstrates a slight rise in the basal levels (greater than 200 nM) (FIG. 8).

After mitogenic stimulation (PHA, 15 microg/ml), the levels of intracellular calcium increase by approximately 70 nM in the control mice and the transgenic mice PS1wt and PS1M146L (FIG. 9). On the other hand, for the mice PS1M5, this increase is 190 nM which is statistically different from the other groups ($p<0.01$). Therefore, not only are the levels of $[Ca^{2+}]_i$ higher under basal conditions, but the clear response to a stimulus is also greater, resulting in much higher absolute levels (400 nM compared with 200-220 nM for the other groups, statistically significant difference).

Furthermore, compared with the nontransgenic controls which exhibit a very rapid calcium response, the latent period to reach the $[Ca^{2+}]i$ peak after stimulation with PHA is greatly increased in the lymphocytes of the PS1M5 transgenics and to a lesser degree for the PS1M146Ls (FIG. 10) but not in the PS1wts.

The differences in the levels and kinetics of calcium responses in the lymphocytes demonstrate a substantial alteration of the processes of mobilization of the intracellular calcium reserves due to the expression of multimutant PS1 in this model.

The alteration of the kinetics of the calcium responses had been previously demonstrated in the lymphocytes of AD patients, which reinforces the relevance of this animal model.

Example 8

Study of the Metabolism of the Free Radicals in the Brain

To confirm the relevance, relative to Alzheimer's disease, of the deficiencies observed in the transgenic mice of the invention, it was investigated if pathological impairments were identifiable in the brain of these animals. In particular, the mechanisms for protection against free radicals were analysed since the latter are involved in the apoptosis phenomena linked to the presenilins and since an impairment in the lymphocytes of PS1M5 transgenic mice was demonstrated in Example 6.

Figure 11A:
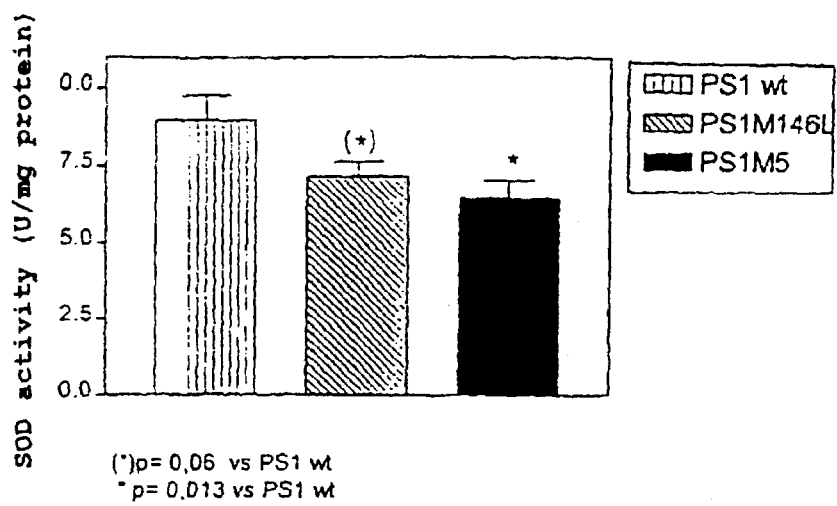

The analyses were carried out on 3-4-month-old animals. Compared with the transgenic mice PS1wt, the PS1M146Ls demonstrate a reduction in the levels of SOD activity by approximately 20% in the brain (FIG. 11A). This reduction is further accentuated in the PS1M5 transgenics (−28%, p<0.05).

Figure 11B:
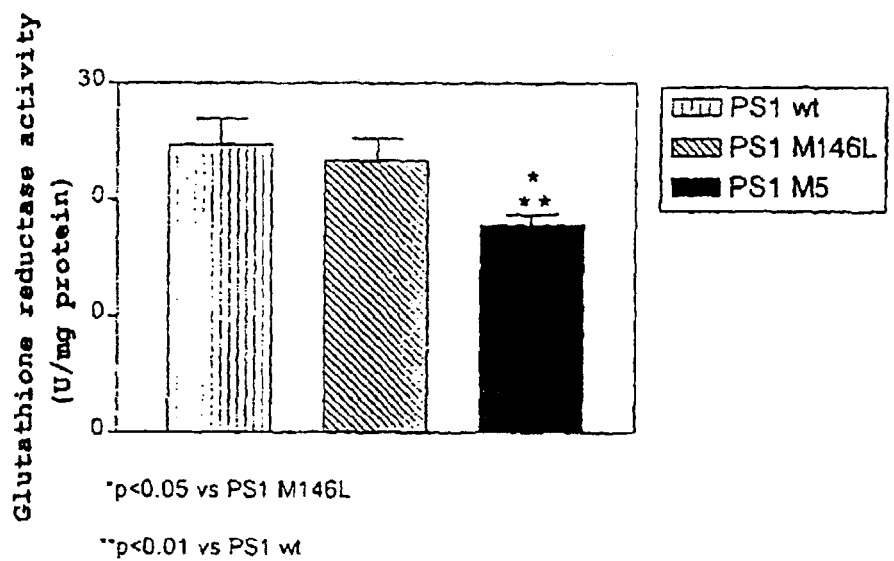
Figure 11C:
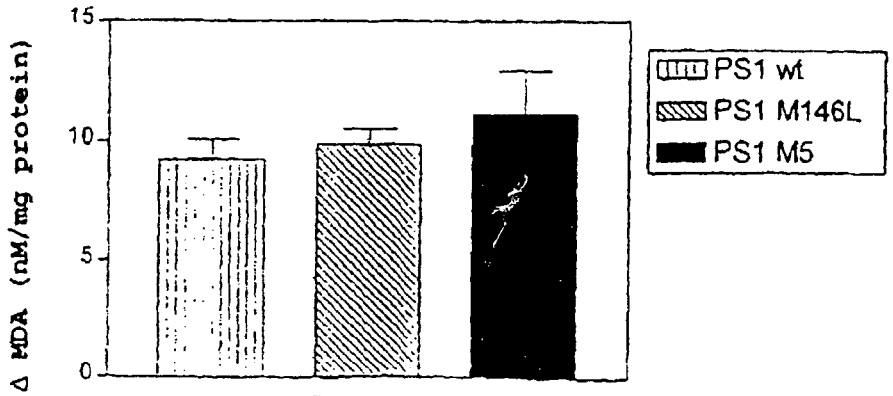

The glutathione reductase activity is also significantly reduced in the brain of the PS1M5 transgenics (~27%, p<0.05). By contrast, a truly modest reduction in this activity modest effect is noted in the PS1-M146L transgenics (FIG. 11B).

The basal lipid peroxidation levels were identical in all the groups of mice. After stimulation with $FeCl_3$, on the other hand, the lipid peroxidation levels are increased in the PS1M5 transgenics (+20%, FIG. 11C).

In multimutated PS1M5 transgenic young adults (3-4 months), a deficiency is therefore observed in the mechanisms for protection from free radicals and in parallel an increase in sensitivity to lipid peroxidation in the brain. This effect perfectly correlates with the increased sensitivity to apoptosis, the impairments in the mobilization of intracellular calcium and the increase in the levels of oxygenated free radical species observed in the lymphocytes of these transgenics which artificially express the transgene in these two tissues. The deficiency in the mechanisms for protection against free radicals was also revealed in patients suffering from Alzheimer's disease, thus confirming the relevance of this animal model.

REFERENCES

Chui, D-H, Tanahashi, H., Ozawa, K., Ikeda, S., Checker, F., Ueda, O., Suzuki, H., Araki, W., Inoue, H., Shirotani, K., Takahashi, K., Gallyas, F. and Tabira, T. (1999) Transgenic mice with Alzheimer presenilin 1 mutations show accelerated neurodegeneration without amyloid plaque formation. *Nature Medicine* 5: 560-564.

Czech, C., Delaere, P., Macq, A.-F., Reibaud, M., Dreisler, S., Touchet, N., Schomber, B., Mazadier, M., Mercken, L., Theisen, M., Pradier, L., Octave, J.-N., Beyreuther, K. and Tremp, G. L. (1997) Proteolytical processing of mutated human amyloid protein precursor in transgenic mice. *Mol. Brain Res.* 47, 108-116.

Czech, C., Lesort, M., Tremp, G., Terro, F., Blanchard, V., Schombert, B., Carpentier, N., Dreisler, S., Bonici, B., Takashima, A., Moussaoui, S., Hugon, J. and Pradier, L. (1998) Characterization of human presenilin 1 transgenic rats: increased sensitivity to apoptosis in primary neuronal cultures. *Neuroscience* 87, 325-36.

Eckert, A., Fórst, H., Zerfass, R., Hennerici, M. and Müller, W E. (1997) Free intracellular calcium in peripheral cells in Alzheimer's Disease. *Neurobiol. Aging* 18: 281-284.

Eckert, A., Fórst H., Zerfass, R., Oster, M., Hennerici, M. and Múller, W E. (1998) Changes in intracellular calcium regulation in Alzheimer's Disease and vascular dementia. *J. Neural. Transm.* (Suppl.) 53: 259-267

Gautier, C., Methali, M. and Lathe, R. (1989) A ubiquitous mammalian expression vector, pHMG, based on a housekeeping gene promoter. *Nucleic. Acids. Res.* 17, 8398

Luthi, A., Putten, H., Botteri, F. M., Mansuy, I. M., Meins, M., Frey, U., Sansig. G., Portet, C., Schmutz, M., Schroder, M., Nitsch, C., Laurent, J. P. and Monard, D. (1997) Endogenous serine protease inhibitor modulates epileptic activity and hippocampal long-term potentiation. *J. Neurosci* 17, 4688-99.

Pradier, L., Carpentier, N., Delalonde, L., Clavel, N., Bock, M.-D., Buéel, L., Mercken, L., Tocqué, B. and Czech, C. (1999) Mapping the APP/presenilin (PS) binding domains: the hydrophilic N-terminus of PS2 is sufficient for interaction with APP and can displace APP/PS1 interaction. *Neurobiol. Dis.* 6, 43-55. Price DL and Sisodia SS (1998). Mutant genes in familial Alzheimer's disease and transgenic models. *Annu. Rev. Neurosci.* 21: 479-505.

Sasahara, M., Fries, J. W., Raines, E. W., Gown, A. M., Westrum, L. E., Frosch, M. P., Bonthron, D. T., Ross, R. and Collins, T. (1991) PDGF B-chain in neurons of the central nervous system, posterior pituitary, and in a transgenic model. *Cell* 64, 217-27.

Scott, M. R., Kohler, R., Foster, D. and Prusiner, S. B. (1992) Chimeric prion protein expression in cultured cells and transgenic mice. *Protein Sci.* 1, 986-97.

Sherrington, R., Rogaev, E. I., Liang, Y., Rogaeva, E. A., Levesque, G., Ikeda, M., Chi, H., Lin, C., Li, G., Holman, K. et al. (1995) Cloning of a gene bearing missense mutations in early-onset familial Alzheimer's disease. *Nature* 375, 754-60.

Yankner B A (1996). Mechanisms of neuronal degeneration in Alzheimer's disease. *Neuron.* 16: 921-932.

What is claimed is:

1. A method for selecting candidate compounds intended for reducing or preventing apoptosis in T lymphocytes comprising:
   (a) exposing said compounds to a first cell extracted from a transgenic mouse expressing a multimutated form of presenilin 1, wherein the mutations are M146L, H163R, A246E, L286V and C410Y,
   (b) comparing the apoptosis level in the first cell to the apoptosis level in a second cell not exposed to said candidate compounds, and
   (c) selecting candidate compounds that reduce or prevent apoptosis.

2. A method for selecting candidate compounds intended for reducing or preventing apoptosis in T lymphocytes comprising:
   (a) exposing said candidate compounds to a first transgenic mouse expressing a multimutated form of presenilin 1, wherein the mutations are M146L, H163R, A246E, L286V and C410Y, (b) comparing the apoptosis level of T lymphocytes from the first mouse to the apoptosis level of T lymphocytes from a second mouse not exposed to said candidate compounds, and (c) selecting candidate compounds that reduce or prevent apoptosis.

* * * * *

UNITED STATES PATENT AND TRADEMARK OFFICE
CERTIFICATE OF CORRECTION

PATENT NO.      : 8,492,610 B1
APPLICATION NO. : 10/088139
DATED           : July 23, 2013
INVENTOR(S)     : Eckert et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 931 days.

Signed and Sealed this
Eighth Day of September, 2015

Michelle K. Lee
*Director of the United States Patent and Trademark Office*

SEQUENCE LISTING

<160> NUMBER OF SEQ ID NOS: 7

<210> SEQ ID NO 1
<211> LENGTH: 21
<212> TYPE: DNA
<213> ORGANISM: Artificial
<220> FEATURE:
<223> OTHER INFORMATION: Construct

<400> SEQUENCE: 1
gaggatagtc gtgacaacaa t                                        21

<210> SEQ ID NO 2
<211> LENGTH: 21
<212> TYPE: DNA
<213> ORGANISM: Artificial
<220> FEATURE:

```
<223> OTHER INFORMATION: Construct

<400> SEQUENCE: 2
aagccaggcc tggatgacct t                                              21

<210> SEQ ID NO 3
<211> LENGTH: 21
<212> TYPE: DNA
<213> ORGANISM: Artificial
<220> FEATURE:
<223> OTHER INFORMATION: Construct

<400> SEQUENCE: 3
gatgagccat gcagtccatt g                                              21

<210> SEQ ID NO 4
<211> LENGTH: 21
<212> TYPE: DNA
<213> ORGANISM: Artificial
<220> FEATURE:
<223> OTHER INFORMATION: Construct

<400> SEQUENCE: 4
ggagtaaatg cgagctggaa a                                              21

<210> SEQ ID NO 5
<211> LENGTH: 21
<212> TYPE: DNA
<213> ORGANISM: Artificial
<220> FEATURE:
<223> OTHER INFORMATION: Construct

<400> SEQUENCE: 5
ggctacgaat caggctatgg t                                              21

<210> SEQ ID NO 6
<211> LENGTH: 19
<212> TYPE: DNA
<213> ORGANISM: Artificial
<220> FEATURE:
<223> OTHER INFORMATION: Primer

<400> SEQUENCE: 6
taattggtcc ataaaaggc                                                 19

<210> SEQ ID NO 7
<211> LENGTH: 21
<212> TYPE: DNA
<213> ORGANISM: Artificial
<220> FEATURE:
<223> OTHER INFORMATION: Primer

<400> SEQUENCE: 7
gcacagaaag ggagtcacaa g                                              21
```